US008045996B2

(12) United States Patent
Brunner et al.

(10) Patent No.: US 8,045,996 B2
(45) Date of Patent: Oct. 25, 2011

(54) DETERMINATION OF CELL RF PARAMETERS BASED ON MEASUREMENTS BY USER EQUIPMENTS

(75) Inventors: Christopher Brunner, San Diego, CA (US); Jay F. Dills, San Diego, CA (US); Jose Edson Vargas Bautista, San Diego, CA (US); Raymond A. Skirsky, San Diego, CA (US); Zoltan Biacs, San Mateo, CA (US); Wyatt Thomas Riley, Wayne, PA (US)

(73) Assignee: QUALCOMM Incorporated, San Diego, CA (US)

( * ) Notice: Subject to any disclaimer, the term of this patent is extended or adjusted under 35 U.S.C. 154(b) by 1120 days.

(21) Appl. No.: 11/830,657

(22) Filed: Jul. 30, 2007

(65) Prior Publication Data

US 2008/0096566 A1 Apr. 24, 2008

Related U.S. Application Data

(60) Provisional application No. 60/834,375, filed on Jul. 31, 2006.

(51) Int. Cl.
*H04W 24/00* (2009.01)
(52) U.S. Cl. ........... 455/456.1; 455/436; 455/437; 455/438; 455/439; 455/440; 455/441; 455/442; 455/443; 455/444; 455/456.2; 455/456.3; 455/456.4; 455/456.5; 455/456.6
(58) Field of Classification Search .......... 455/436, 455/437, 438, 439, 440, 442, 443, 450, 451, 455/452.1, 452.2, 453, 456.1, 456.2, 456.4, 455/456.5, 456.6, 441, 444, 456.3
See application file for complete search history.

(56) References Cited

U.S. PATENT DOCUMENTS 5,386,456 A * 1/1995 Schatz et al. .............. 455/436
(Continued)

FOREIGN PATENT DOCUMENTS

DE    19836778    2/2000
(Continued)

OTHER PUBLICATIONS

"Universal Mobile Telecommunications System (UMTS); User Equipment (UE) Positioning in Universal Terrestrial Radio Access Network (UTRAN); Stage 2 (3GPP TS 25.305 version 7.3.0 Release 7)," pp. 1-81, ETSI TS 125 305 v7.3.0 (Jun. 2006).
Partial International Search Report, PCT/US07/074897, International Search Authority, European Patent Office, May 7, 2008.
International Search Report—PCT/US07/074897—International Search Authority, European Patent Office—Oct. 10, 2008.

(Continued)

*Primary Examiner* — Olumide T Ajibade Akonai
(74) *Attorney, Agent, or Firm* — Ramin Mobarhan (57) ABSTRACT

Techniques for using measurements made by UEs to improve network performance are described. In one aspect, RF parameters of cells may be determined by taking into account mobility of the UEs. Mobility information for the UEs may be determined based on measurement report messages (MRMs) sent by these UEs for handover. RF parameters such as antenna down-tilt, antenna orientation, antenna pattern, and/or pilot power of the cells may be determined based on the mobility information for the UEs. In another aspect, the RF parameters of cells may be dynamically adjusted based on loading conditions of cells. In yet another aspect, the location of a UE may be determined based on an MRM sent by the UE for handover. The MRM may include timing measurements for multiple cells. The location of the UE may be determined based on the timing measurements.

13 Claims, 8 Drawing Sheets

U.S. PATENT DOCUMENTS

| | | | | |
|---|---|---|---|---|
| 5,657,487 A * | 8/1997 | Doner | ........................ | 455/456.2 |
| 5,838,674 A * | 11/1998 | Forssen et al. | ................. | 370/337 |
| 6,104,936 A * | 8/2000 | Kronestedt | ................ | 455/562.1 |
| 6,140,963 A * | 10/2000 | Azzarelli et al. | .............. | 342/442 |
| 6,167,286 A * | 12/2000 | Ward et al. | ................. | 455/562.1 |
| 6,473,619 B1 * | 10/2002 | Kong et al. | ................. | 455/456.1 |
| 6,745,034 B2 * | 6/2004 | Wang et al. | ................... | 455/441 |
| 7,248,897 B2 * | 7/2007 | Hsu | ................ | 455/561 |
| 7,289,834 B2 * | 10/2007 | Sun et al. | .................. | 455/575.5 |
| 7,797,000 B2 * | 9/2010 | Anderson | .................. | 455/456.2 |
| 2003/0148774 A1 * | 8/2003 | Naghian et al. | ............... | 455/456 |
| 2006/0068849 A1 * | 3/2006 | Bernhard et al. | .......... | 455/562.1 |
| 2007/0021085 A1 * | 1/2007 | Kroeger | ........................ | 455/272 |

FOREIGN PATENT DOCUMENTS

| | | |
|---|---|---|
| DE | 10031178 | 1/2002 |
| EP | 1315393 | 5/2003 |
| EP | 1317161 | 6/2003 |
| WO | 03086005 | 10/2003 |
| WO | 03098953 | 11/2003 |
| WO | 2004095868 | 11/2004 |

OTHER PUBLICATIONS

Written Opinion—PCT/US07/074897—International Search Authority, European Patent Office—Oct. 10, 2008.

* cited by examiner

DETERMINATION OF CELL RF PARAMETERS BASED ON MEASUREMENTS BY USER EQUIPMENTS

CLAIM OF PRIORITY UNDER 35 U.S.C. §119

The present application for patent claims priority to Provisional Application Ser. No. 60/834,375, entitled "Automatic RF Optimization With RF Measurements Captured In The UEs," filed Jul. 31, 2006, assigned to the assignee hereof, and expressly incorporated herein by reference.

BACKGROUND

I. Field

The present disclosure relates generally to communication, and more specifically to techniques for utilizing measurements by user equipments (UEs) in a wireless communication network.

II. Background

Wireless communication networks are widely deployed to provide various communication services such as voice, video, packet data, messaging, broadcast, etc. These wireless networks may be multiple-access networks capable of supporting multiple users by sharing the available network resources. Examples of such multiple-access networks include Code Division Multiple Access (CDMA) networks, Time Division Multiple Access (TDMA) networks, Frequency Division Multiple Access (FDMA) networks, Orthogonal FDMA (OFDMA) networks, and Single-Carrier FDMA (SC-FDMA) networks.

A wireless network may include many cells that may support communication for many users. Each cell may be associated with radio frequency (RF) parameters such as antenna down-tilt, antenna orientation, antenna pattern, pilot power, noise floor, etc. The RF parameters of each cell may be set to achieve the desired coverage and capacity for that cell. During a cell planning stage, traffic maps and RF propagation models may be applied to a cell planning tool that may determine the RF parameters of cells to obtain the desired performance. In many instances, the RF parameters may be set sub-optimally due to inaccurate and/or insufficient inputs to the cell planning tool. This may result in sub-optimal network performance, e.g., more dropped calls, more call setup failures, lower throughput, etc.

SUMMARY

Techniques for using measurements made by UEs to improve network performance are described herein. In one aspect, RF parameters of cells may be determined by taking into account mobility of the UEs. Mobility information for the UEs may be determined based on measurement report messages (MRMs) sent by these UEs for handover. RF parameters such as antenna down-tilt, antenna orientation, antenna pattern, pilot power, and/or noise floor of the cells may be determined based on the mobility information for the UEs. The RF parameters may also be determined further based on RF measurements from the UEs, traffic maps, RF propagation models, etc.

In another aspect, RF parameters of cells may be dynamically adjusted based on loading conditions. The loading conditions of the cells may be determined based on the MRMs from the UEs and/or via other means. The RF parameters of the cells may be adjusted based on the loading conditions to improve network performance.

In yet another aspect, the location of a UE may be determined based on an MRM sent by the UE for handover. The MRM may comprise timing measurements for multiple cells. The location of the UE, when the MRM is generated, may be determined based on the timing measurements, which may comprise observed time difference (OTD) measurements. In one design, observed delay differences for the cells may be determined based on the OTD measurements. Relative time differences (RTDs) for the cells may also be determined, e.g., based on RF measurements included in the MRM or a known location of a cell. The location of the UE may then be determined based on the observed delay differences, the known locations of the cells, and the RTDs.

Various aspects and features of the disclosure are described in further detail below.

DETAILED DESCRIPTION

The techniques described herein may be used for various wireless communication networks such as CDMA, TDMA, FDMA, OFDMA and SC-FDMA networks. The terms "network" and "system" are often used interchangeably. A CDMA network may implement a radio technology such as Universal Terrestrial Radio Access (UTRA), cdma2000, etc. UTRA includes Wideband-CDMA (W-CDMA), Low Chip Rate (LCR), High Chip Rate (HCR), etc. cdma2000 covers IS-2000, IS-95, and IS-856 standards. A TDMA network may implement a radio technology such as Global System for Mobile Communications (GSM). An OFDMA network may implement a radio technology such as Evolved UTRA (E-UTRA), Ultra Mobile Broadband (UMB), IEEE 802.11 (Wi-Fi), IEEE 802.16 (WiMAX), IEEE 802.20, Flash-OFDM®, etc. These various radio technologies and standards are known in the art. UTRA, E-UTRA and GSM are described in documents from an organization named "3rd Generation Partnership Project" (3GPP). cdma2000 is described in documents from an organization named "3rd Generation Partnership Project 2" (3GPP2). 3GPP and 3GPP2 documents are publicly available. For clarity, certain aspects of the techniques are described below for 3GPP networks.

Figure 1:
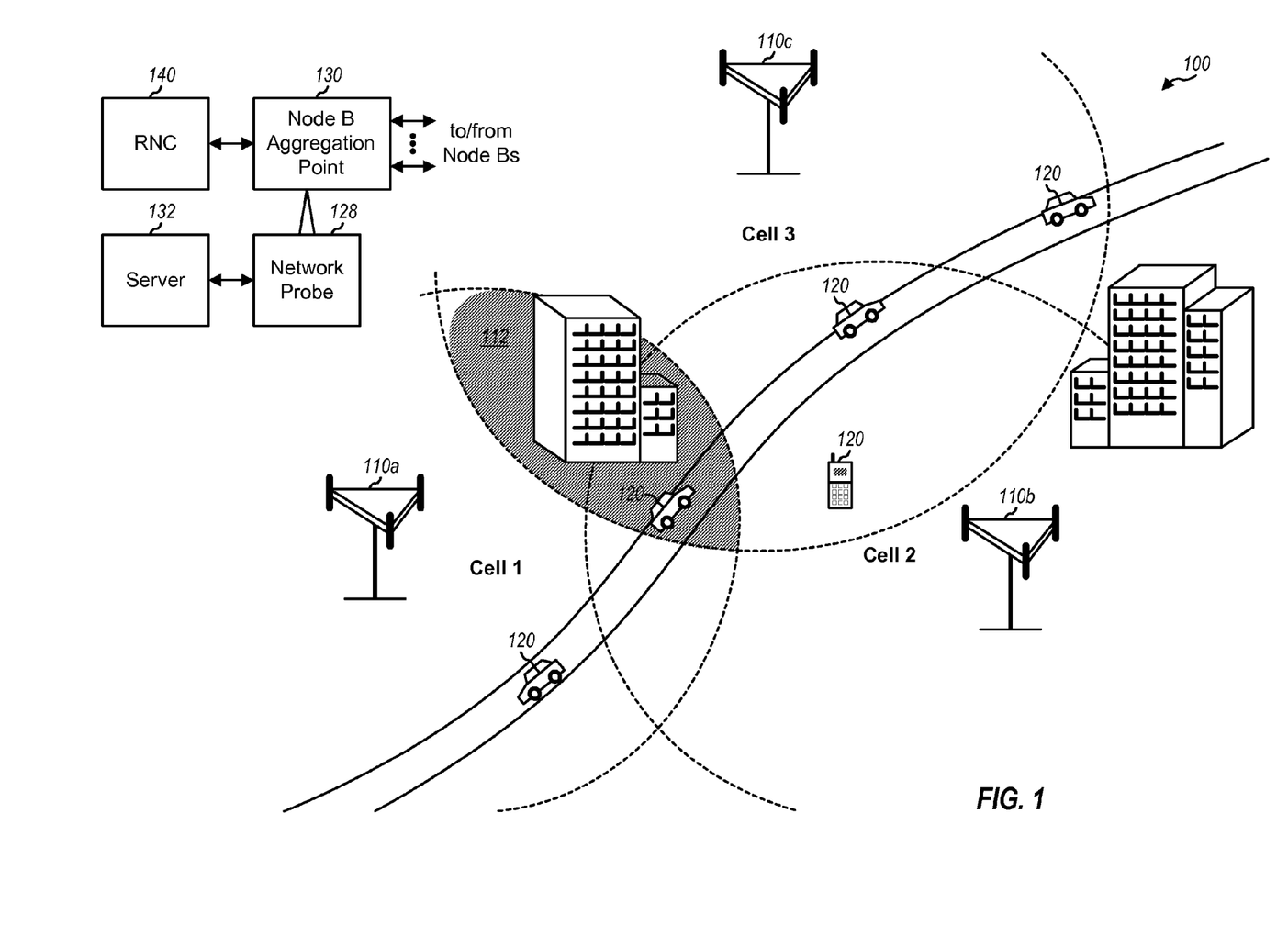
FIG. 1 shows a wireless communication network.

FIG. 1 shows a wireless communication network 100, which may be a Universal Mobile Telecommunication System (UMTS) network that implements W-CDMA. In the example shown in FIG. 1, wireless network 100 includes three Node Bs 110a, 110b and 110c. A Node B is a fixed station that communicates with the UEs and may also be referred to as a base station, an evolved Node B (eNode B), an access point, etc. Each Node B 110 provides communication coverage for a particular geographic area. The coverage area of a Node B may be partitioned into smaller areas, e.g., three smaller areas. The term "cell" can refer to the smallest unit of coverage of a Node B or a Node B subsystem serving this coverage area, depending on the context in which the term is used. In FIG. 1, Node Bs 110a, 110b and 110c serve cells 1, 2 and 3, respectively.

Node Bs 110 may couple to a Node B aggregation point 130, which may aggregate data and signaling for these Node Bs. Aggregation point 130 may further couple to a Radio Network Controller (RNC) 140, which may provide coordination and control for the Node Bs coupled to the RNC via the aggregation point. For example, RNC 140 may perform radio resource management, some mobility management functions, and other functions to support communication for UEs.

UEs 120 may be dispersed throughout the wireless network. A UE may be stationary or mobile and may also be referred to as a mobile station, a mobile equipment, a terminal, an access terminal, a subscriber unit, a station, etc. A UE may be a cellular phone, a personal digital assistant (PDA), a wireless communication device, a handheld device, a wireless modem, etc. A UE may communicate with one or more Node Bs via transmissions on the downlink and uplink. The downlink (or forward link) refers to the communication link from the Node Bs to the UEs, and the uplink (or reverse link) refers to the communication link from the UEs to the Node Bs. The terms "UE" and "user" are used interchangeably herein.

Each cell has a particular coverage area that may be determined based on the RF parameters of that cell. The antenna down-tilt, antenna orientation, and antenna pattern affect RF propagation characteristics and hence the coverage of the cell. The pilot power affects reception of the pilot from the cell by the UEs. Changing pilot power may change the cell size but may cause link imbalance between the downlink and uplink. If the pilot power is adjusted (e.g., reduced), then the noise floor of the cell may be artificially adjusted correspondingly for the uplink (e.g., increased to weaken the uplink) in order to avoid link imbalance.

During a cell planning stage, traffic maps and RF propagation models may be obtained for the network deployment area. The traffic maps may indicate areas where users may be more concentrated and may be obtained in various manners, e.g., by determining the locations of user, by observing traffic in the area, etc. The terms "location" and "position" are synonymous and are used interchangeably herein. The RF propagation models may be used to predict path loss of RF signals and may be based on an Okumura-Hata model or some other model. The cell locations may be known, e.g., due to deployment of UMTS cells at existing GSM cell sites. In this case, the traffic maps, RF propagation models, and cell locations may be provided to a cell planning tool such as Atoll, Planet, Assett, Odyssey, etc., which are known in the art. The cell planning tool may determine the RF parameters of the cells such that good network performance in terms of coverage and capacity may be achieved. Alternatively, the traffic maps and RF propagation models may be provided to an automatic cell planning (ACP) tool such as Radioplan, Schema, Arieso, etc., which are also known in the art. The ACP tool may propose cell sites and determine the RF parameters such that good network performance may be achieved.

In an aspect, cell planning may be performed by taking into account mobility of users. Wireless network 100 may be deployed over an existing wireless network, e.g., a GSM network. Relatively accurate traffic maps may be obtained based on information for users in the existing network and their locations. The user locations may be determined based on positioning capabilities of the existing network, which may be used to support E-911 related requirements. Traffic maps may also be obtained in other manners, e.g., by observing users in the geographic area and noting their approximate locations. Relatively accurate mobility maps may be obtained based on information for the users in the existing network and locations where handovers occur. Mobility maps may also be obtained in other manners, e.g., by observing the users in the geographic area and their changing locations.

The traffic maps and RF propagation models may be provided to a cell planning tool and used to determine site locations and RF parameter settings for new cells to be deployed. Existing cell sites may be reused for new cells, and new cell site locations may be selected from among the existing cell sites. The cell planning tool may select cell site locations and RF parameter settings based on a tradeoff between coverage and capacity. The mobility maps may be used for cell planning in various manners.

In one design, a performance metric may be defined as a function of coverage, capacity, and mobility and may be used to select cell site locations and/or RF parameter settings. The performance metric may be a function of the number of handovers at cell boundaries, which may be estimated based on the mobility maps. For example, the mobility maps may indicate locations where the UEs send measurement report messages (MRMs) to request handover to new cells. The number of handovers may be estimated based on the number of MRMs sent by the UEs. It may be desirable to select cell site locations and RF parameter settings such that the number of handovers may be reduced. Frequent handovers of UEs in idle mode (which are referred to as cell reselections) may drain UE battery and degrade call setup performance. Frequent handovers of UEs in active mode may adversely impact real-time services such as voice and video streaming and further reduce service coverage for the wireless network.

The cell site locations and RF parameter settings may be selected to reduce the number of handovers and to provide "clean" cell boundaries. The boundary between two cells A and B may be considered as clean if, while moving from cell A to cell B, the pilot from cell A becomes weaker monotonically and the pilot from cell B becomes stronger monotonically, and there is one cross-over point for the pilots from the two cells. The boundary between multiple cells may be considered as "not clean" if these cells are received equally strong and/or take turn being strong in different spots at the cell boundary. This phenomenon is also commonly referred to as "pilot pollution" and may result in frequent and possibly fast handovers between the cells. Clean cell boundaries and hence no/low pilot pollution may be obtained by selecting cell site locations and/or RF parameter settings such that one or few pilots are dominant. This may be desirable especially in areas with higher concentration of users and/or more mobile users.

In the example shown in FIG. 1, three cells 1, 2 and 3 may have overlapping coverage in an area 112. Area 112 may have a relatively high concentration of mobile users, which may be indicated by the traffic maps and mobility maps. This may result in frequent handovers of the users in area 112 among the three cells 1, 2 and 3.

Figure 2:
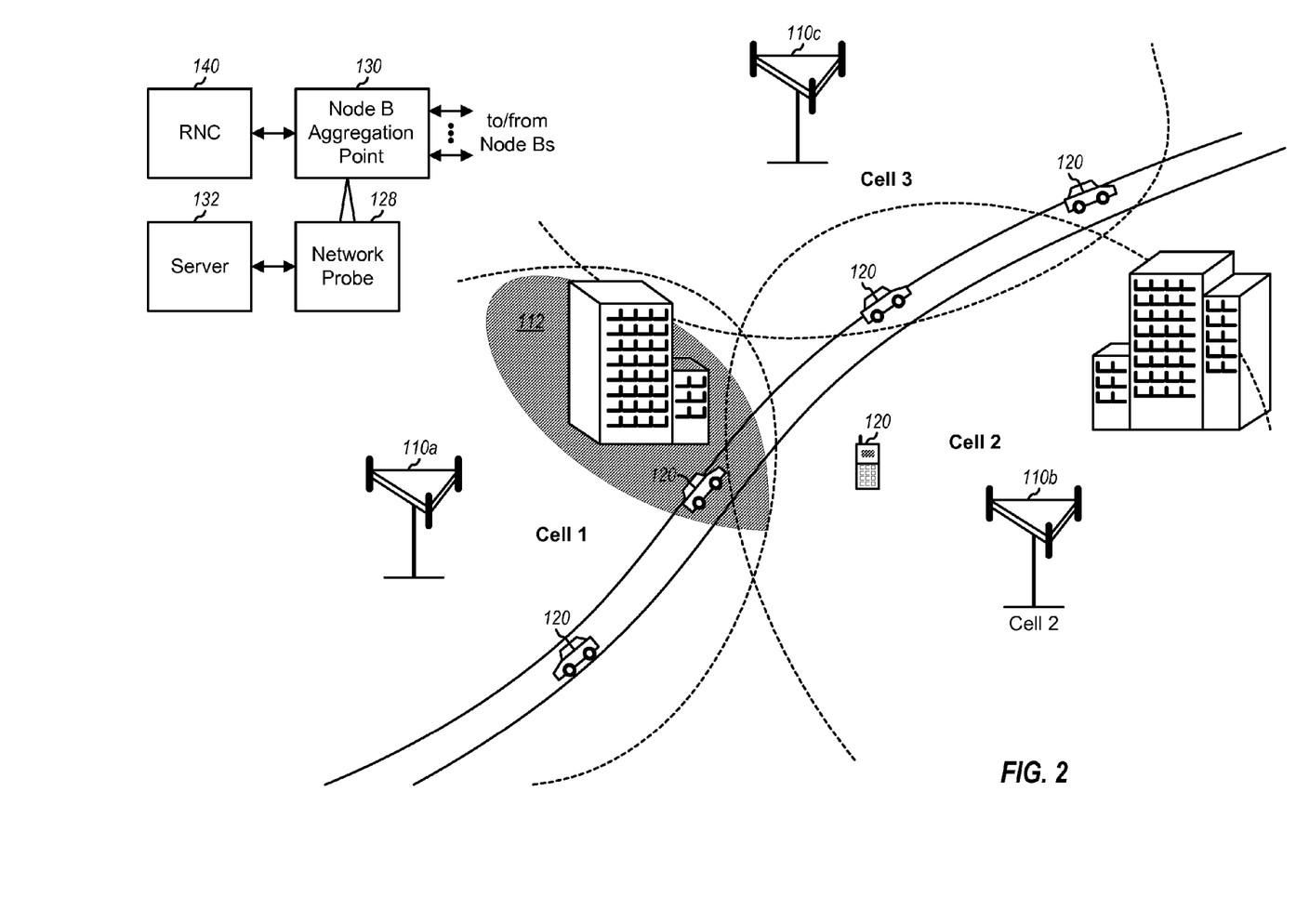
FIG. 2 shows adjustment of cell coverage by adjusting RF parameters of cells.

FIG. 2 shows an example of using traffic maps and mobility maps to adjust cell coverage. In this example, the coverage of cells 1, 2 and 3 may be adjusted by selecting appropriate RF parameters for these cells such that there are fewer and possibly cleaner cell boundaries. This may result in fewer handovers of the users in area 112.

In general, traffic maps and mobility maps may be used to select good cell site locations, to reduce the number of cell boundaries, to place the cell boundaries such that fewer handovers may occur, etc. Clean cell boundaries may be obtained for an area with dense user population by placing a cell in the area or by pointing a cell at the area. Clean cell boundaries may be more important for high mobility users since less time may be available for handovers. Reducing the number of handovers may provide certain advantages such as less handover-related signaling, fewer cell reselections in idle mode (which may extend UE battery life), improved performance (e.g., fewer dropped calls) in active mode, etc. The RF parameters may be set such that good RF performance may be targeted at high user density areas and/or high usage areas while weak RF performance may be moved to less frequented areas. The RF parameters may also be set to reduce pilot pollution, quickly changing serving cells, coverage holes, etc.

The results from cell planning tools are typically only as good as the inputs (e.g., traffic maps, RF propagation models, and mobility maps) provided to these tools. The inputs may be relatively coarse in many instances. For example, traffic data may be coarse and available only at cell level. Furthermore, service areas of different types of services may not be taken into account. The RF propagation models may also be inaccurate for various reasons. Drive testing may be performed to measure RF conditions at different locations, and these RF measurements may be used to fine-tune the RF propagation models. The revised RF propagation models may then be applied to the cell planning tools to update the RF parameters of the cells, which may improve network performance. However, drive testing may be time consuming and typically covers only streets but not indoors.

In another aspect, after deployment, the RF parameters of cells may be adjusted based on measurements made by the UEs in the wireless network. A UE may make measurements for cells in an active set, a neighbor set, and/or a detected set. The active set may include cells that are currently serving the UE. The neighbor/candidate set may include cells that the UE can be handed over. The detected set may include cells that the UE detected with sufficient pilot strength or quality. The UE may generate and send an MRM, which may contain the following:

RF measurements for cells—may be used to trigger handover of the UE, and

Timing measurements for the cells—may be used for downlink synchronization during handover of the UE.

The RF measurements may be for pilot strength, pilot quality, etc. Pilot strength may be indicative of the received pilot power at the UE and may also be referred to as received signal code power (RSCP). Pilot quality may be indicative of the quality of the received pilot at the UE, which takes into account the received pilot power as well as interference. Pilot quality may also be referred to as energy-per-chip-to-total-noise ratio (Ec/No). The UE may also obtain other types of measurement such as received signal strength indicator (RSSI), signal-to-interference ratio (SIR), etc. For simplicity, the following description assumes the use of RSCP and Ec/No. The timing measurements may be given in various formats, as described below.

The UE may obtain RSCP measurements and/or Ec/No measurements for any number of cells, e.g., cells in the active, neighbor, and/or detected set. The UE may also obtain timing/synchronization information for these cells. The UE may send the measurements and the associated timing information in an MRM, e.g., to the serving cell or the RNC. The RSCP measurements may be used to compute path-loss and to build accurate RF maps. The Ec/No measurements may indicate load/interference on the downlink and may be used to build accurate load maps. The UE may generate and send MRMs periodically or when triggered. Since the MRMs contain timing information for cells and an identifier of the UE (UE ID), the location of the UE may be ascertained based on the measurements as described below. Furthermore, the MRMs may be used to determine the mobility of the UE and may be used to construct mobility maps.

Figure 3:
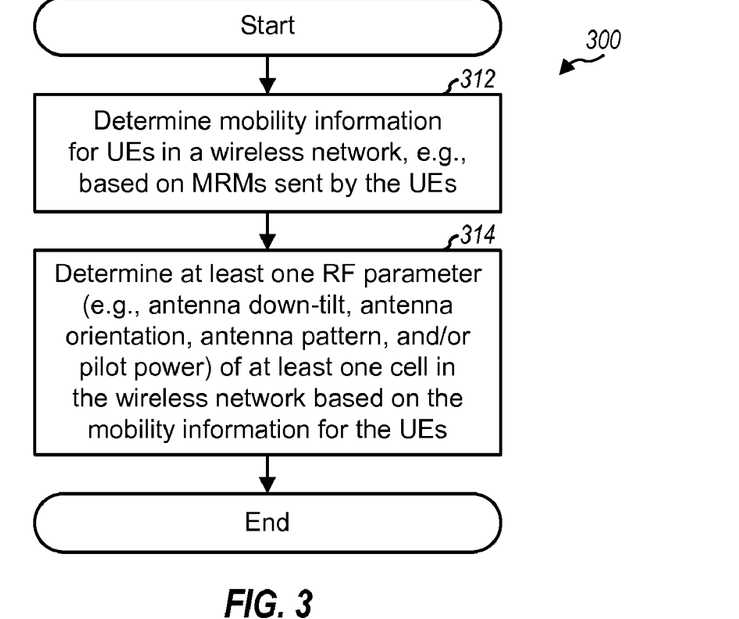
FIG. 3 shows a process to adjust RF parameters by taking into account mobility.

FIG. 3 shows a design of a process 300 for determining RF parameters of cells by taking into account mobility of UEs. Mobility information for UEs may be determined, e.g., based on MRMs sent by these UEs for handover (block 312). For example, the locations of the UEs may be determined based on the MRMs as described below, and the mobility information may be determined based on the UE locations. The mobility information may indicate the locations of the UEs during handover.

At least one RF parameter (e.g., antenna down-tilt, antenna orientation, antenna pattern, pilot power, noise floor, etc.) of at least one cell may be determined based on the mobility information for the UEs (block 314). The RF parameter(s) may also be determined further based on RF information for the UEs, traffic information, RF propagation information, etc. The RF information may be determined based on the MRMs, which may include pilot strength measurements, pilot quality measurements, etc. The RF parameter(s) may be adjusted to have stronger coverage in certain areas, to move coverage boundary, to reduce pilot pollution, to increase coverage, to increase capacity, to reduce or move coverage holes, etc. The RF parameter(s) may be adjusted to achieve good network performance in terms of tradeoff between coverage, capacity, and mobility, e.g., to reduce the number of handovers in active mode and the number of cell reselections in idle mode.

In one design, MRMs collected from UEs may be processed to estimate the UE locations and to identify RF issues such as pilot pollution, overshooting cells, excessive interference, and coverage and capacity limitations. These RF issues may cause call drops, call setup failures, low throughput, etc. The RF parameters of cells may then be set based on the identified RF issues and taking into account the UE locations as well as estimation errors in the UE locations. The effect of changes in antenna down-tilt, antenna orientation, and/or pilot power on the RF issues may be modeled, e.g., using a cell planning tool. The UE locations may be sufficiently accurate to forecast the delta in cell antenna gain caused by a change in antenna down-tilt or orientation. Probability density functions (PDFs) of the delta in cell antenna gain resulting from a change in antenna down-tilt or orientation may be calculated based on the estimated UE locations, the average inaccuracy of the positioning scheme, the cell site configuration, etc. The RF parameters may then be adjusted to minimize an appropriate cost function based on the delta in cell antenna gain PDFs for the estimated UE locations. RF changes that further weaken areas of weak RF (based on coverage and maximum load across the area) may be prevented by selecting appropriate confidence levels.

In one design, a simple line-of-site (LOS) model may be used as an RF propagation model to compute the change in cell antenna gain caused by a change in RF parameters. In a macro-cellular environment, most of the scattering may take place in close proximity of the UEs. Thus, a LOS model may be sufficient. Slow and fast fading caused by scattering and multi-path may be taken into account by using RF measurements from the UEs. In one design, RF measurements of previous settings may be stored and reused if old RF parameter settings are evaluated.

In yet another aspect, the RF parameters of cells may be dynamically adjusted based on loading conditions of the cells the wireless network. The loading conditions may be ascertained based on MRMs from the UEs, scheduling information, etc. The RF parameters may be adjusted dynamically to achieve good network performance while maintaining the same or similar coverage.

Figure 4:
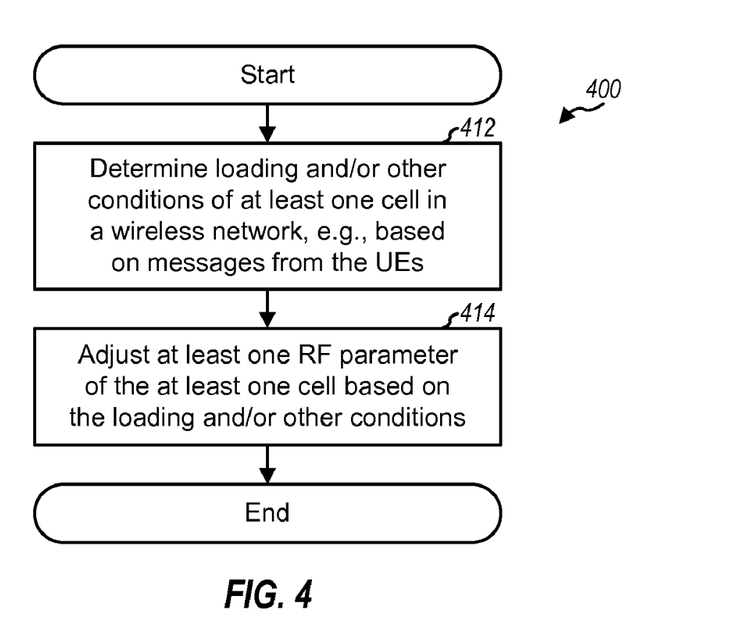
FIG. 4 shows a process to adjust RF parameters based on loading conditions.

FIG. 4 shows a design of a process 400 for adjusting RF parameters based on loading conditions. The loading and/or other conditions of at least one cell in the wireless network may be determined, e.g., based on messages from the UEs (block 412). For example, the UEs may send messages to report mobility information (e.g., location), RF conditions (e.g., RSCP and Ec/Io), performance (e.g., throughput and BLER), etc. These messages may be MRMs and/or other types of messages. The UEs may send these messages for various purposes such as handover, location reporting, network performance monitoring and tuning, etc. The messages from the UEs may be used to determine loading conditions and/or other conditions of the at least one cell. At least one RF parameter of the at least one cell may be adjusted based on the loading and/or other conditions (block 414).

The UEs may send MRMs during normal operation to support handover. Timing measurements in these MRMs may be used to determine the locations of the UEs, which may be used to adjust the RF parameters of the cells. The timing measurements for UMTS may be generated as described below.

Figure 5:
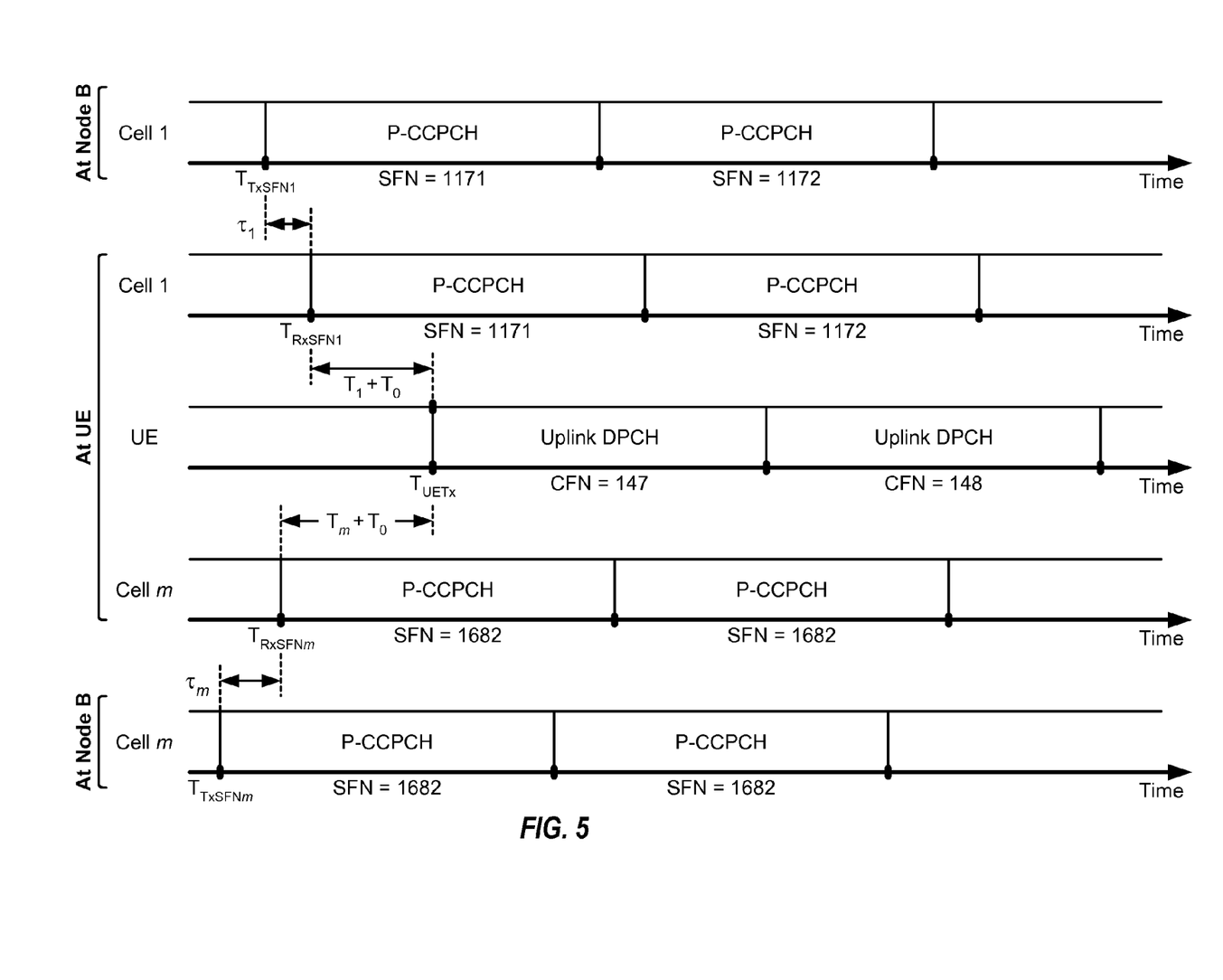
FIG. 5 shows timing of a UE and two cells.

FIG. 5 shows an example of the timing of a UE and two cells in wireless network 100. In UMTS, the transmission timeline of each cell is partitioned into frames, with each frame having a duration of approximately 10 milliseconds (ms) and covering 38,400 chips. Each frame is identified by a 12-bit system frame number (SFN). The SFN is incremented by one for each frame, ranges from 0 to 4095, and wraps around to 0 after reaching 4095. The SFN is sent every 20 ms on a Primary Common Control Physical Channel (P-CCPCH). In UMTS, the cells may operate asynchronously. In this case, the frames of different cells may not be time-aligned and may also have different frame numbering, as shown in FIG. 5.

The transmission timeline of the UE is also partitioned into frames, with each frame being identified by an 8-bit connection frame number (CFN). The CFN is initialized based on the SFN of a serving cell when a Dedicated Physical Channel (DPCH) is established for the UE. The CFN is maintained by the UE and the RNC and is not sent over the air.

The UE may determine an SFN-CFN observed time difference (OTD) for a given cell m, as follows:

$$OTD_m = OFF_m \cdot 38,400 + T_m \qquad \text{Eq (1)}$$

where
$OTD_m$ is the OTD for cell m,
$OFF_m$ is a frame-level portion of the OTD for cell m, and
$T_m$ is a chip-level portion of the OTD for cell m.
$OTD_m$ is the difference between the timing of cell m and the timing of the UE, as observed by the UE and given in units of chip. The chip-level portion of the OTD may be given as:

$$T_m = (T_{UETx} - T_0) - T_{RxSFNm} \qquad \text{Eq (2)}$$

where
$T_{UETx}$ is the start of an uplink DPCH frame for the UE,
$T_0$ is a constant defined to be equal to 1024 chips, and
$T_{RxSFNm}$ is the start of a P-CCPCH frame for cell m before time instant $T_{UETx} - T_0$, as observed at the UE.
Time instant $T_{UETx} - T_0$ is the start of a downlink DPCH frame for the serving cell. The start of the uplink DPCH frame for the UE is set $T_0$ chips after the start of the downlink DPCH frame, as measured at the UE. Time instant $T_{UETx}$ is used as a time reference to measure $T_m$ for each cell to be reported.

The frame-level portion of the OTD may be given as:

$$OFF_m = (SFN_m - CFN_{Tx}) \bmod 256 \qquad \text{Eq (3)}$$

where
$CFN_{Tx}$ is the CFN of the uplink DPCH frame starting at time $T_{UETx}$, and
$SFN_m$ is the SFN of the P-CCPCH frame for cell m starting at time $T_{RxSFNm}$.
As shown in FIG. 5, the UE receives the P-CCPCH frame for cell m after a delay of $\tau_m$, which is the propagation delay from cell m to the UE. The P-CCPCH frame is transmitted by cell m at time instant $T_{TxSFNm}$ and is received by the UE at time instant $T_{RxSFNm}$, where $\tau_m = T_{TxSFNm} - T_{RxSFNm}$.

The UE may make RF and OTD measurements for any number of cells. The UE may send these measurements in an MRM to the serving cell. The OTD measurements and possibly the RF measurements may be used to determine the location of the UE when the MRM is generated, which is also referred to as "positioning the MRM". Since the UE may be at different locations for different MRMs, the positioning may be performed for each MRM.

Figure 6:
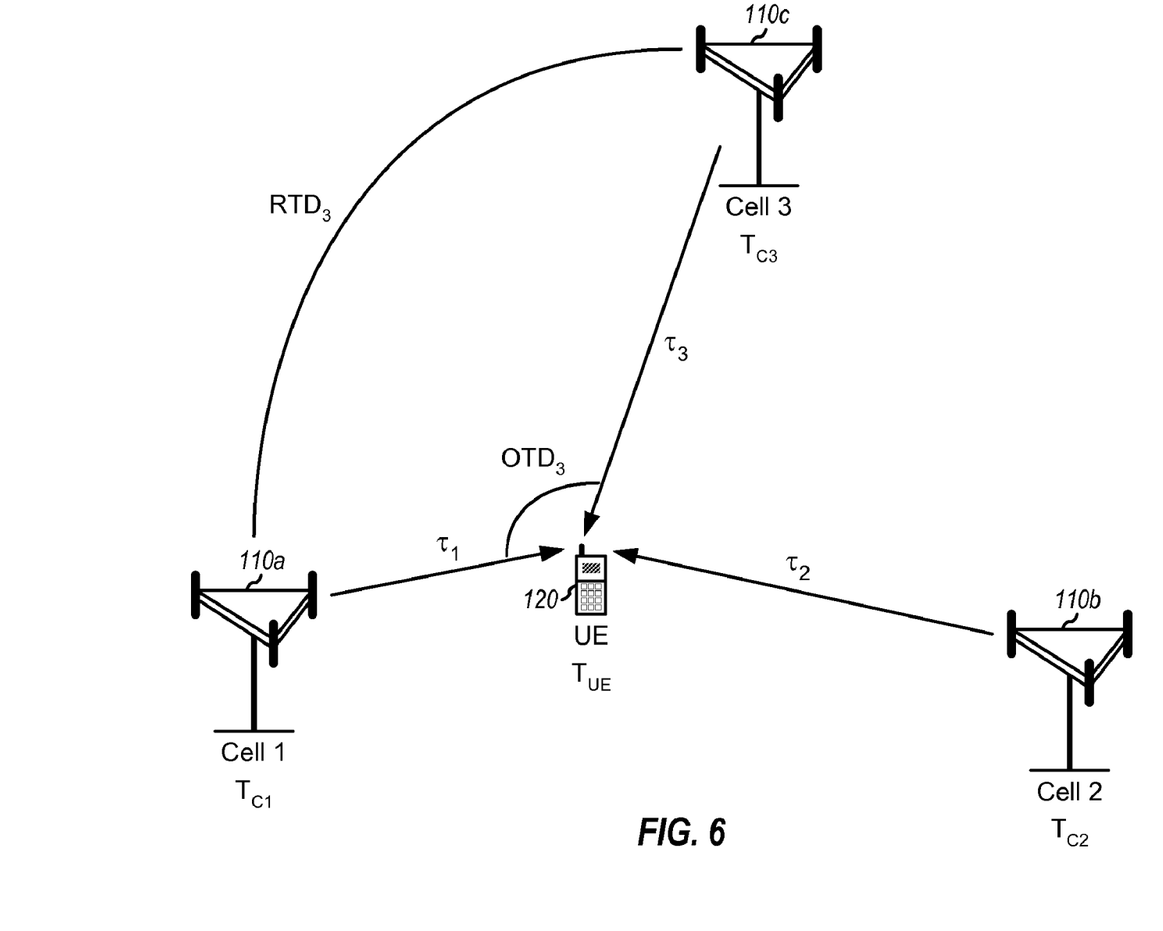
FIG. 6 shows a system model for the UE and three cells.

FIG. 6 shows a system model for one UE and three cells 1, 2 and 3. The UE may obtain SFN-CFN OTD measurements for the three cells, as described above. These OTD measurements may be expressed as:

$$OTD_1 = T_{UE} - (T_{C1} + \tau_1),$$

$$OTD_2 = T_{UE} - (T_{C2} + \tau_2), \text{ and}$$

$$OTD_3 = T_{UE} - (T_{C3} + \tau_3) \qquad \text{Eq (4)}$$

where
$T_{UE}$ is the time reference at the UE, which may correspond to $T_{UETx} - T_0$,
$T_{C1}$, $T_{C2}$ and $T_{C3}$ are time references for cells 1, 2 and 3, respectively,
$\tau_1$, $\tau_2$ and $\tau_3$ are propagation delays for cells 1, 2 and 3, respectively, and
$OTD_1$, $OTD_2$ and $OTD_3$ are OTDs for cells 1, 2 and 3, respectively.

As shown in equation set (4), the OTDs are measurements of the timing of the cells as observed at the UE and include the propagation delays for these cells. Relative time differences (RTDs) between the cells may be defined as:

$$RTD_{21} = T_{C2} - T_{C1} = OTD_1 - OTD_2 - (\tau_2 - \tau_1) = OTD_1 - OTD_2 - \delta_{21},$$

$$RTD_{31} = T_{C3} - T_{C1} = OTD_1 - OTD_3 - (\tau_3 - \tau_1) = OTD_1 - OTD_3 - \delta_{31} \qquad \text{Eq (5)}$$

where
$\delta_{21}$ and $\delta_{31}$ are observed time difference of arrival (OTDOA) for cells 2 and 3, respectively, relative to cell 1, and
$RTD_{21}$ and $RTD_{31}$ are RTDs for cells 2 and 3, respectively, relative to cell 1.

In equation set (5), the OTDs may be known from the MRM, and the RTDs and OTDOAs may be determined as described below. The RTDs may also be referred to as timing relations. The OTDOAs may also be referred to as observed delay differences.

The measurements in the MRM may be used to determine the location of the UE for that MRM, or simply, the MRM location. The MRM may provide OTDs between the MRM location and several cells (typically between two to eight cells) and RF measurements for these cells. The locations of the cells may be known. These different types of information may be used to position the MRM.

In one design, the MRM location may be estimated as follows:
  A1. Determine timing relations or RTDs between the cells, e.g., based on a bootstrap technique, and
  A2. Estimate the MRM location based on the RTDs and OTDs, e.g., with an iterative algorithm.

Steps A1 and A2 may be performed as described below.

In one design of step A1, the timing relations between the cells reported in the MRM may be determined as follows:
  B1. Estimate the distance between the MRM location and each cell based on an RF measurement for the cell and an RF propagation/path-loss model,
  B2. Estimate the MRM location based on the estimated distances to the cells,
  B3. Estimate the propagation delay of each cell based on the MRM and cell locations, and
  B4. Determine the RTDs between the cells based on the propagation delays.

For step B1, the path loss of each cell reported in the MRM may first be determined as follows:

$$L_m = P_m + A_m(x,y) - RSCP_m \qquad \text{Eq (6)}$$

where
  $P_m$ is the pilot power of cell m,
  $A_m(x, y)$ is an antenna gain of cell m as a function of the MRM location (x, y),
  $RSCP_m$ is the RSCP of the pilot from cell m, and
  $L_m$ is the path loss of cell m, in units of decibel (dB).

The antenna gain $A_m(x, y)$ may be computed based on a base station almanac and line-of-sight (LOS) assumption.

The distance between the MRM location and each cell may then be estimated based on the path loss of the cell and the RF propagation model, as follows:

$$\hat{r}_m = 10^{\left(\frac{L_m - \Gamma}{10 \cdot n}\right)}, \qquad \text{Eq (7)}$$

where
  n is a path loss exponent, which may be set to n=3.84,
  $\Gamma$ is a path loss constant that may be set to $\Gamma$=138.5 dB, and
  $\hat{r}_m$ is the estimated distance to cell m based on the RSCP measurement.

For step B2, the MRM location may be estimated based on the estimated distances to the cells obtained from step B1. If the estimated distances have no errors, then they would intersect at a single point, which may be provided as the MRM location. However, the estimated distances will likely have errors, and the MRM location may be determined to minimize the errors.

Figure 7:
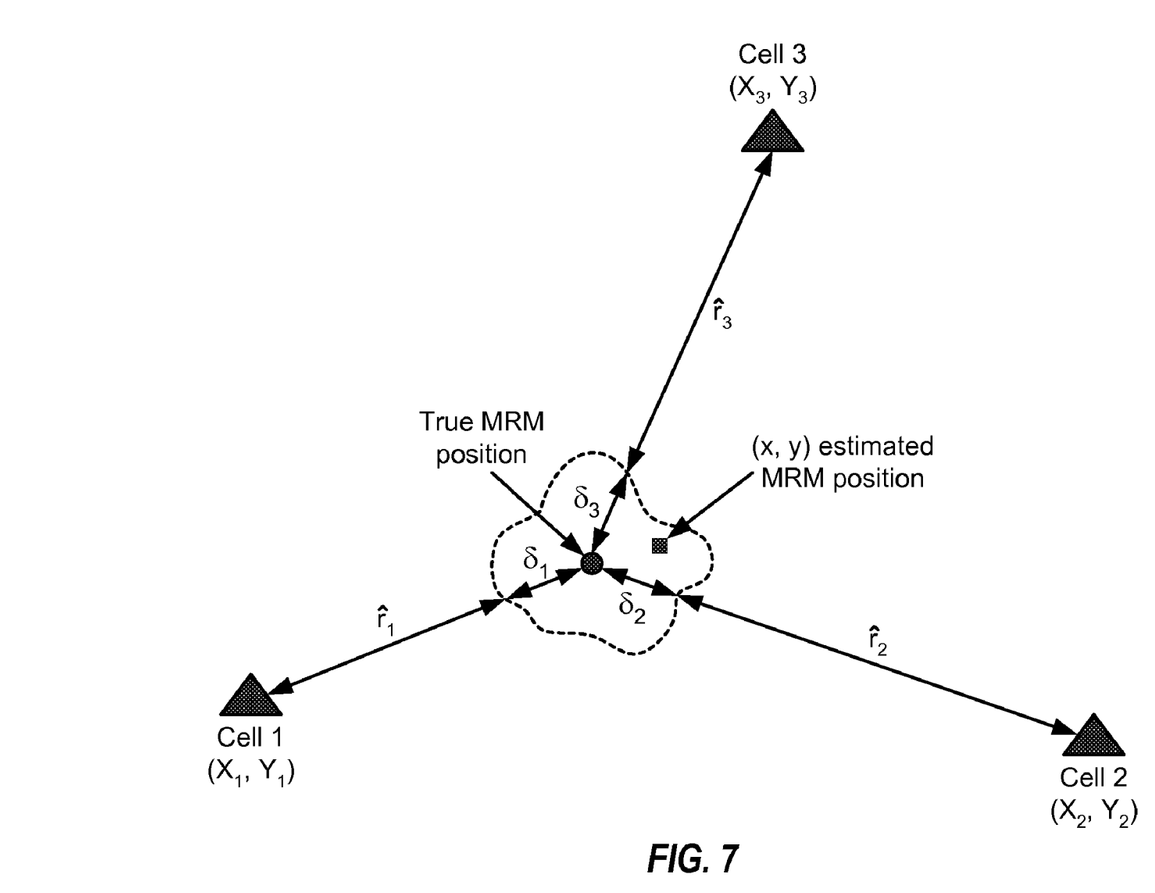
FIG. 7 shows trilateration to estimate the location of the UE.

FIG. 7 shows an example of trilateration to estimate the MRM location based on the estimated distances to the cells. For simplicity, the following description assumes 2-dimensional (2D) coordinates with longitude and latitude, e.g., (x, y) for the MRM location and $(X_m, Y_m)$ for the location of cell m. In general, coordinates may be given in 2D as noted above or in 3-dimensional (3D) with longitude, latitude, and elevation, e.g., (x, y, z) for the MRM location. In the example shown in FIG. 7, cells 1, 2 and 3 are located at coordinates $(X_1, Y_1)$, $(X_2, Y_2)$ and $(X_3, Y_3)$, respectively, which are known. The MRM location is at coordinates (x, y), which is to be estimated. The computed distance between cell m and the MRM location (x, y) may be expressed as:

$$r_m = \sqrt{(X_m - x)^2 + (Y_m - y)^2} = \sqrt{X_m^2 + x^2 - 2xX_m + Y_m^2 + y^2 - 2yY_m}, \qquad \text{Eq (8)}$$

where $r_m$ is the computed distance between the MRM location and cell m.

The MRM location may be determined such that the differences between the estimated and computed distances to the cells are minimized. This may be achieved by minimizing the following error metric:

$$E(x, y) = \sum_{m=1}^{M} |r_m^2 - \hat{r}_m^2| \qquad \text{Eq (9)}$$

$$= \sum_{m=1}^{M} |X_m^2 + x^2 - 2xX_m + Y_m^2 + y^2 - 2yY_m - \hat{r}_m^2|$$

where E(x, y) is an error metric and M is the number of cells in the MRM.

Equation (9) may be used if the MRM contains measurements for three or more cells. If measurements for less than three cells are included in the MRM, then there is ambiguity in the MRM location. Furthermore, since antenna gain $A_m(x, y)$ is a function of the MRM location, equations (6) to (9) may be iterated multiple times to minimize the error metric E(x, y). The MRM location may be obtained after completing all of the iterations.

For step B3, the distance between the MRM location obtained from step B2 and each cell may be computed as shown in equation (8). The distance to each cell may then be converted to propagation delay, as follows:

$$\tau_m = r_m / C \qquad \text{Eq (10)}$$

where
  C is signal propagation speed, which is $C \approx 3 \times 10^8$, and
  $\tau_m$ is the propagation delay from cell m to the MRM location, as shown in FIG. 6.

For step B4, the timing relations between the cells may be computed as follows:

$$RTD_{mi} = OTD_i - OTD_m - (\tau_m - \tau_i) \qquad \text{Eq (11)}$$

where $RTD_{mi}$ is the RTD for cell m relative to reference cell i. One cell in the MRM may be used as reference cell i, and the RTD may be computed for each remaining cell in the MRM. Reference cell i may be the serving cell, the strongest cell, the earliest cell, etc. In equation (11), the OTDs may be from the MRM, and the propagation delays may be obtained from step B3.

Multiple (K) MRMs may be received from the UE. The RTDs may be computed for the cells reported in each MRM. The RTDs then may be averaged over the K MRMs to improve the accuracy of the RTD estimates, as follows:

$$RTD_{mi,avg} = \sum_{k=1}^{K} W_k \cdot RTD_{mi,k}, \qquad \text{Eq (12)}$$

where

RTD$_{mi,k}$ is the RTD for cells m and i for the k-th MRM,
W$_k$ is a weight for the k-th MRM, and
RTD$_{mi,avg}$ is the average RTD for cells m and i for the K MRMs.

Equation (12) shows one scheme of averaging over multiple MRMs. The averaging may also be performed in other manners. In another scheme, the median RTD$_{mi,k}$ may be selected instead of the mean and provided as RTD$_{mi,avg}$. In yet another scheme, a mapping function may attenuate measurements that are far from the median. In any case, averaging over multiple MRMs may improve accuracy by smoothing the effects of shadowing and fast fading. Weight W$_k$ may be selected to give more weight to more reliable RTDs. For example, a more accurate estimate of the MRM location may be obtained from an MRM with more cells, and the RTDs obtained from this MRM may be given more weight. The duration of the averaging may be limited such that clock drifts at the cells are negligible.

In another design of step A1, the timing relations between the cells may be determined based on a coarse estimate of the MRM location. For example, the location of the serving cell, the strongest cell, the earliest cell, or some other cell may be used as the coarse estimate of the MRM location. As another example, the coverage center of the serving cell, the strongest cell, the earliest cell, or some other cell may be used as the coarse estimate of the MRM location. As yet another example, a random starting location may be used as the coarse estimate of the MRM location. In any case, the coarse estimate of the MRM location may be used to determine a coarse distance to each cell, as shown in equation (8). The coarse distance may then be converted to a coarse propagation delay, as shown in equation (10). The RTDs for pairs of cells may then be derived as shown in equations (11) and (12).

Cells belonging to the same Node B typically have time offsets that are fixed and most likely known. This information may be exploited in several ways. First, the number of unknowns may be reduced and more measurements may be available to estimate these unknowns, which may improve accuracy. Second, only the first multipath may be considered, and signal components arriving at different cells of the same Node B with delay may be discarded.

For step A2, the location of an MRM may be estimated based on an iterative algorithm, as follows:

C1. Compute the MRM location based on the OTD measurements in the MRM,
C2. Estimate the distances between the MRM location and the cell locations and convert the distances to propagation delays,
C3. Determine the timing relations between the cells based on the propagation delays, and
C4. Quit if the MRM location converge, or return to step C1 otherwise.

For step C1, the observed delay difference may first be estimated for each non-reference cell m as follows:

$$\hat{\delta}_{mi} = \tau_m - \tau_i = OTD_i - OTD_m - RTD_{mi} \qquad \text{Eq (13)}$$

where

RTD$_{mi}$ may be set to RTD$_{mi,avg}$ obtained from step B4 for the first iteration, and
$\hat{\delta}_{mi}$ is the observed delay difference between cell m and reference cell i.

A relative pseudo-range may then be computed for each non-reference cell, as follows:

$$\hat{\Delta}_{mi} = \hat{\delta}_{mi} \cdot C = r_m - r_i \qquad \text{Eq (14)}$$

where $\hat{\Delta}_{mi}$ is the relative pseudo-range between cell m and reference cell i.

In equation (14), $\hat{\Delta}_{mi}$ may be computed for each non-reference cell. $r_m$ and $r_i$ are unknowns and are dependent on the MRM location (x, y), as shown in equation (8). At least two relative pseudo-ranges (e.g., $\hat{\Delta}_{21}$ and $\hat{\Delta}_{31}$) may be determined and used to estimate the MRM location. If two relative pseudo-ranges are available, then the MRM location may be computed based on a closed form solution, e.g., described by Y. T. Chan and K. C. Ho in a paper entitled "A Simple And Efficient Estimator for Hyperbolic Location," IEEE Trans. Signal Proc., Vol. 42, No. 8, August 1994. If more than two relative pseudo-ranges are available, then the MRM location may be computed based on an iterative technique such as least mean square (LMS), linear minimum mean square error (LMMSE), recursive least square (RLS), etc. The LMS and RLS techniques are described by Simon Haykin in a book entitled "Adaptive Filter Theory", 3rd edition, Prentice Hall, 1996. In any case, two or more equations for relative pseudo-ranges may be used to compute the two unknowns x and y for the MRM location.

For step C2, the distance $r_m$ between the MRM location obtained from step C1 and each cell may be computed as shown in equation (8). The distance $r_m$ to each cell may then be converted to propagation delay $\tau_m$, as shown in equation (10).

For step C3, the timing relations RTD$_{mi}$ between the cells may be computed based on the propagation delays $\tau_m$ obtained from step C2 and the OTDs from the MRM, as shown in equation (11). The RTDs obtained from the OTD measurements in step C3 may be more accurate than the initial RTDs obtained from the RF measurements in step B4. The RTDs for the cells may be averaged over multiple MRMs, e.g., as shown in equation (12).

For step C4, the change in the MRM location between the current and last iteration may be determined. If the change is below a threshold, then convergence may be declared, and the MRM location from the current iteration may be provided as the final estimate of the MRM location. If the change exceeds the threshold, then another iteration may be performed starting at step C1.

For clarity, a specific design for estimating the MRM location based on SFN-SFN OTD measurements has been described above. The MRM location may also be estimated based on other timing measurements and/or with other positioning techniques. The design described above estimates 2D coordinates (x, y) of the MRM location. 3D coordinates (x, y, z) of the MRM location may be estimated in similar manner, albeit with an additional unknown for elevation z. Elevation at the estimated MRM location may also be obtained via Google Earth map or some other techniques.

In another design, the UE may report Type 1 SFN-SFN OTD measurements for cells. In this design, the frame-level portion of the Type 1 SFN-SFN OTD may be given as:

$$OFF_m = SFN_i - SFN_m \qquad \text{Eq (15)}$$

where SFN$_i$ and SFN$_m$ are the SFNs of reference cell i and non-reference cell m, respectively.

The chip-level portion of the Type 1 SFN-SFN OTD may be given as:

$$T_m = T_{RxSFNm} - T_{RxSFNi} \qquad \text{Eq (16)}$$

where

T$_{RxSFNm}$ is the start of a P-CCPCH frame for non-reference cell m, and
T$_{RxSFNi}$ is the start of a P-CCPCH frame for reference cell i.

In yet another design, the UE may report Type 2 SFN-SFN OTD measurements for cells. In this design, the chip-level portion of the Type 2 SFN-SFN OTD may be given as:

$$T_m = T_{CPICHRxm} - T_{CPICHRxi} \qquad \text{Eq (17)}$$

where $T_{CPICHRxm}$ is the start of a P-CPICH frame received from cell m, and $T_{CPICHRxi}$ is the start of a P-CPICH frame received from cell i.

For the system model shown in FIG. 6, the Type 2 SFN-SFN OTD measurements may be defined as:

$$\text{OTDS}_{21} = (T_{C2} + \tau_2) - (T_{C1} + \tau_1), \text{ and}$$

$$\text{OTDS}_{31} = (T_{C3} + \tau_3) - (T_{C1} + \tau_1) \qquad \text{Eq (18)}$$

where $\text{OTDS}_{mi}$ is a time difference perceived by the UE between cell m and cell i as captured by the SFN. $\text{OTDS}_{21}$ and $\text{OTDS}_{31}$ may be OTD measurements sent in the MRM when reporting Type 2 SFN-SFN.

The observed delay differences may be given as:

$$\delta_{21} = \tau_2 - \tau_1 = \text{OTDS}_{21} - \text{RTD}_{21}, \text{ and}$$

$$\delta_{31} = \tau_3 - \tau_1 = \text{OTDS}_{31} - \text{RTD}_{31} \qquad \text{Eq (19)}$$

The observed delay differences from equation (19) may be used to estimate the MRM location, e.g., as described above.

The UE may also report measurements for UE Rx-Tx time difference, measurements for UE GPS timing of cell frames for UE positioning, measurements for round trip time (RTT), measurements for UTRAN GPS timing of cell frames for UE positioning, etc. The SFN-CFN measurements, Type 1 SFN-SFN measurements, Type 2 SFN-SFN measurements, and other measurements are described in 3GPP TS 25.215, entitled "Physical layer—Measurements (FDD)," May 5, 2007, which is publicly available.

Figure 8:
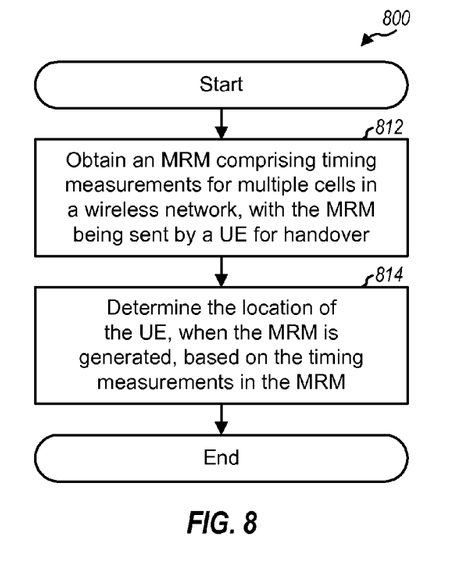
FIG. 8 shows a process to estimate the location of the UE based on an MRM.

FIG. 8 shows a design of a process 800 for estimating MRM location. An MRM comprising timing measurements for multiple cells may be obtained, with the MRM being sent by a UE for handover or when triggered (block 812). For example, the UE may be configured to periodically send MRMs, which may be used by the wireless network to assess general coverage and/or for other purposes. The timing measurements may comprise SFN-CFN OTD measurements, SFN-SFN OTD measurements for Type 1 or 2, etc. The location of the UE, when the MRM is generated, may be determined based on the timing measurements in the MRM (block 814). For block 814, observed delay differences $\hat{\delta}_{mi}$ for the cells in the MRM may be determined based on the timing measurements. RTDs for the cells may also be determined, e.g., based on the RF measurements included in the MRM, a known location of a cell, etc. The location of the UE may then be determined based on the observed delay differences, the known locations of the cells, and the RTDs, as described above.

MRMs may be collected from the UEs in the wireless network. The location of each MRM containing measurements for a sufficient number of cells may be determined as described above. Load/traffic maps and mobility maps may be generated based on the locations of the MRMs. RF maps may also be generated based on the RF measurements in the MRMs. These various maps may be applied to cell planning tools and used to adjust the RF parameters of cells in order to improve network performance. In particular, the RF parameters of cells may be adjusted based on a performance metric that may be a function of coverage, capacity, and mobility, as noted above.

The use of MRMs for RF parameter adjustment may be advantageous for a number of reasons. First, the MRMs are sent for normal UE operation and thus no additional overhead may be incurred to obtain these MRMs. Second, the MRMs provide measurements covering areas "where paying customers go" and including areas that may not be accessible to drive test vans (e.g., indoors) and areas with low user density. The ability to capture indoor users via MRMs may provide more accurate RF modeling for indoor, which may be beneficial because indoor links tend to be weaker than outdoor links. Third, the UEs may be triggered to send MRMs based on downlink and uplink channel metrics in order to support intra-frequency, inter-frequency, and inter-system handover. Hence, measurements with location may be available in weak areas where RF optimization may be more beneficial. Various other benefits may also be obtained through the use of MRMs for RF parameter adjustment.

An active set may be maintained for a UE and may include one or more serving cells for the UE. In UMTS, a new cell may be added to the active set if the following condition occurs for a predetermined time period:

$$\text{Pilot\_Ec/No} > \text{Best\_Pilot\_Ec/No} - \text{Reporting\_Range} + \text{Hysteresis\_Event1A} \qquad \text{Eq (20)}$$

where Pilot_Ec/No is for the new cell, Best_Pilot_Ec/No is for the best cell in the active set, Reporting_Range is a threshold for handover, and Hysteresis_Event1A is a cell addition hysteresis.

An existing cell may be removed from the active set if the following condition occurs for a predetermined time period:

$$\text{Pilot\_Ec/No} < \text{Best\_Pilot\_Ec/No} - \text{Reporting\_Range} + \text{Hysteresis\_Event1B} \qquad \text{Eq (21)}$$

where Hysteresis_Event1B is a cell removal hysteresis.

The reporting range and hysteresis may be set by the wireless network and applied for all cells to be added or removed from the active set.

In yet another aspect, the MRMs from the UEs may be used to determine cell individual offsets (CIOs), which may be parameters affecting handover. The CIOs may be used to trigger the UEs to send MRMs for handover. The CIOs may also be used to add cells to the active sets of the UEs.

A wireless network may be deployed in an area with bad topology, e.g., a seaside city with large open water body, tall skyscrapers, hills, etc. In such an area, pilot pollution may be prevalent and may be difficult to improve even with proper cell planning. A mobile UE may observe rapidly changing RF conditions for different cells within a small area. If cells are not added to the active set fast enough in such a scenario, then dropped calls may be common.

CIOs may be used to allow cells to be added to the active set of a UE faster in a scenario with pilot pollution. The CIOs may be used to adjust the offset used to add cells in the active set, so that cells can be added earlier. The CIOs may be defined to be applicable for only certain active set composition, or to differ for different active set compositions, etc. For example, the CIOs may be defined such that certain cells may be added sooner in a particular area where pilot pollution is prevalent, and this particular area may be ascertained based on the presence of certain cells. Various rules may be used to determine the CIOs. For example, a measurement report of Type 1A or 1C (to add or swap a cell) may be received first, followed by a measurement report of Type 2D or 1F (to leave W-CDMA). This scenario may indicate that the cell is added or swapped too late, and the CIO may be set so that the cell may be added sooner.

The use of CIOs may allow for tailoring of handover performance across the wireless network. For example, the handover reporting range may be reduced across a large area in order to reduce the average number of cells in the active sets and to reduce network resources to support soft handover. CIOs may be used in areas with pilot pollution to ensure early inclusion of cells in active sets so that call retention performance may be improved.

In yet another aspect, the MRMs from the UEs may be used to determine inter-system handover threshold settings at the cell level. The inter-system handover threshold settings may be determined based on network environment, e.g., coverage holes, outdoor to indoor scenarios, coverage boundaries, etc. The inter-system handover thresholds may be lower in coverage holes than in outdoor to indoor scenarios in order to trigger handover earlier in coverage holes and to achieve constant call drop rates. The inter-system handover thresholds may also be set to reduce inter-system handover in UMTS coverage. The inter-system handover thresholds for cell reselection during idle mode may also be set to achieve good call setup performance, to extend UMTS coverage, and to improve battery life. For example, if there is pilot pollution in UMTS that cannot be improved via RF parameter adjustment, then inter-system cell reselection and handover thresholds may be set such that handover to GSM is triggered early, and GSM mobility thresholds may be set such that the UEs stays in GSM. Conversely, if UMTS coverage is clean, then inter-system cell reselection and handover thresholds may be set aggressively to favor handover to UMTS.

Figure 9:
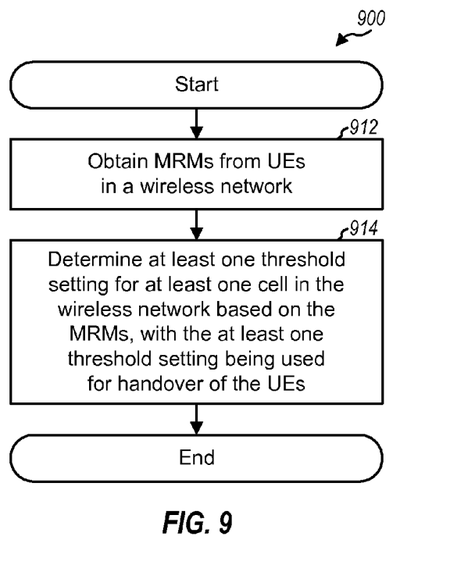
FIG. 9 shows a process to automatically determine threshold settings with MRMs.

FIG. 9 shows a design of a process 900 for using MRMs to automatically determine threshold settings. MRMs from UEs in a wireless network may be obtained (block 912). At least one threshold setting for at least one cell in the wireless network may be determined based on the MRMs, with the at least one threshold setting being used for handover of the UEs (block 914). The at least one threshold setting may comprise at least one CIO used to add the at least one cell in the active sets of the UEs. Alternatively or additionally, the at least one threshold setting may comprise at least one inter-system handover threshold setting used to select the at least one cell for inter-system handover. The least one threshold setting may be determined to reduce the number of handovers for the UEs, to reduce the number of dropped calls, to improve call setup performance, etc.

In yet another aspect, the MRMs from the UEs may be used to set the pilot power levels of cells. The MRMs may be used to identify areas with pilot pollution. The pilot power of one or more cells in the area may be adjusted to reduce pilot pollution.

The MRMs from the UEs may be captured or collected in various manners. In one design, the MRMs may be captured in the wireless network with the use of network probes. A network probe is a device that collects data in a wireless network for performance monitoring and/or other purposes.

Referring back to FIG. 1, Node Bs 110 may receive MRMs from UEs and may forward these MRMs to RNC 140 via Node B aggregation point 130. RNC 140 may use the MRMs to make handover decisions for the UEs and/or for other purposes. Node Bs 110 may interface with RNC 140 via IuB interfaces, which may be aggregated before entering the RNC. A network probe 128 may be installed in (or attached to) Node B aggregation point 130 and used to capture the MRMs of entire wireless network 100 under load. Network probe 128 may provide the MRMs to a server 132, which may process the MRMs to derive load/traffic maps, RF maps, mobility maps, etc. and/or to adjust RF parameters of cells. Network probe 128 may already be used for network performance monitoring and/or other functions and may thus be able to capture the MRMs with small incremental cost. Network probe 128 may be any commercially available network probe such as GeoProbe from Tektronix, Inc. The MRMs may also be collected in other manners, e.g., using Telnet on the RNC.

In UMTS, 512 primary scrambling codes (PSCs) are defined and may be used to distinguish the downlink transmissions of different cells. If only these 512 PSCs are used in a wireless network, then the MRMs may be attributed to unique cells based on the PSCs. If more than 512 PSCs are used, then the MRMs may not be attributable to unique cells based solely on the PSCs. In this case, a relation may be established between cell IDs of PSCs of a Node B and a Node B ID. When collecting MRMs with a network probe, the cell IDs may be assigned to the PSCs based on the Node B ID. The reporting of cell IDs in MRMs may be activated. The MRMs of a UE (which may be identified by its temporary IMSI) may be collected for a particular duration after capturing a cell ID, e.g., at connection setup for the UE. The neighbor lists of the UE may be tracked by capturing measurement control messages, e.g., the neighbor lists may identify sets of Node Bs uniquely with large probability.

Figure 10:
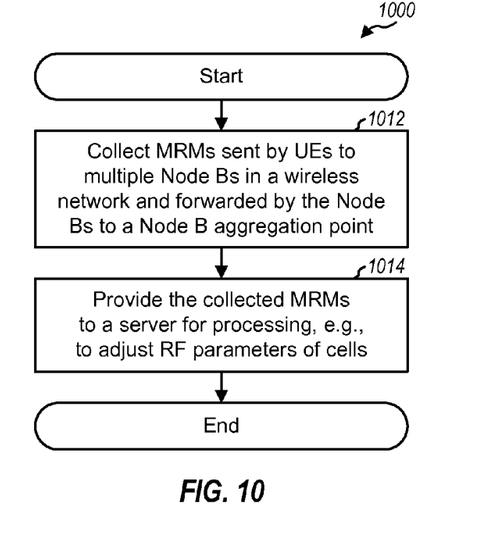
FIG. 10 shows a process to collect MRMs using a network probe.

FIG. 10 shows a design of a process 1000 for collecting MRMs. MRMs sent by UEs to multiple Node Bs in a wireless network and forwarded by the Node Bs to a Node B aggregation point may be collected, e.g., with a network probe (block 1012). The collected MRMs may be provided to a server for processing (block 1014). The MRMs may be sent by the UEs for handover and may be used to adjust RF parameters of cells served by the Node Bs.

In another design, MRMs may be captured by having the UEs send these MRMs to a designated server, e.g., server 132. An application running on the UEs (e.g., Mobile View) may capture the MRMs and send them over the air to the server. The server may then process the MRMs to obtain the load/traffic maps, RF maps, mobility maps, etc. and/or to adjust RF parameters of cells.

Figure 11:
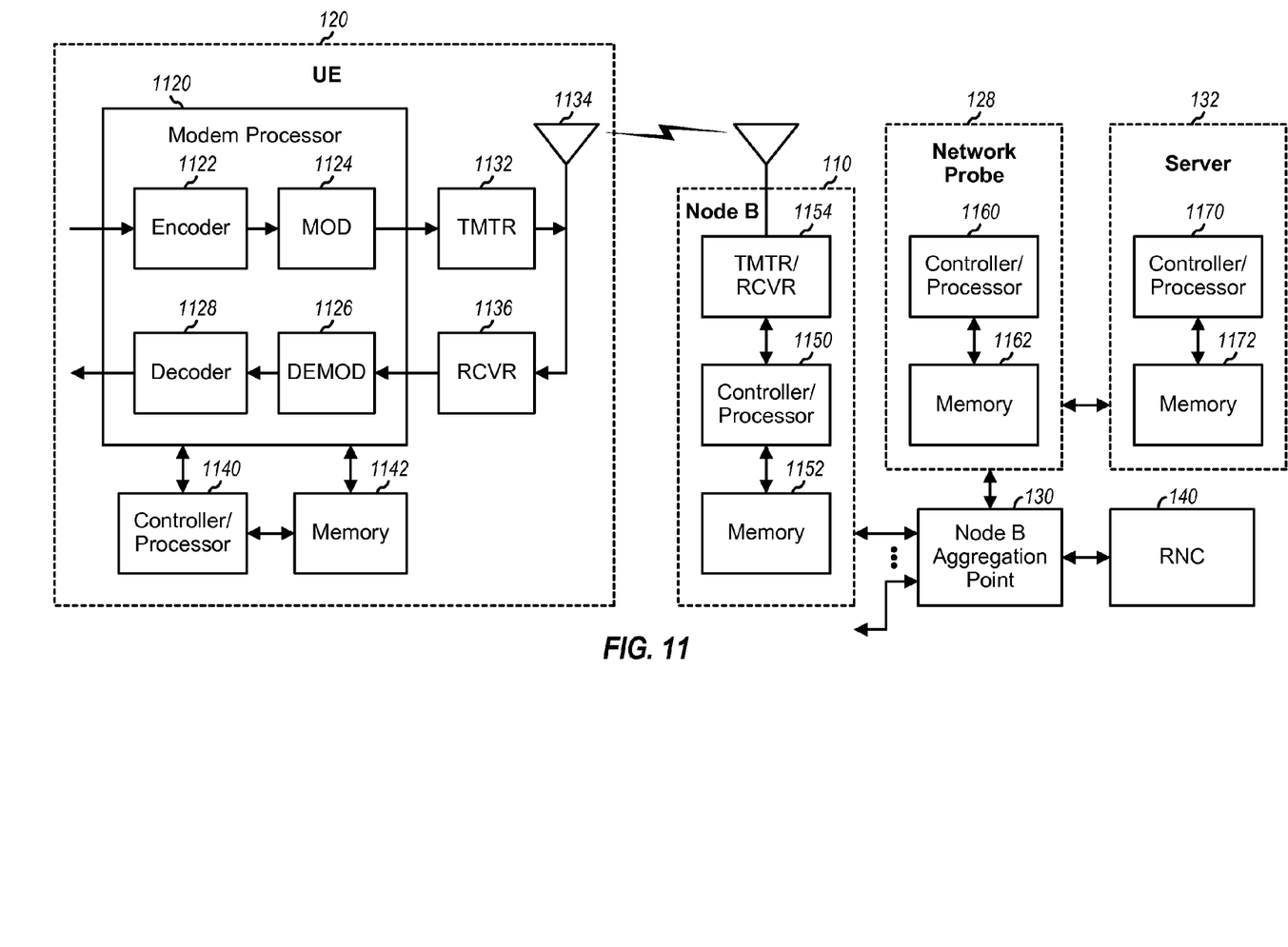
FIG. 11 shows a block diagram of the UE and other entities.

FIG. 11 shows a block diagram of a design of UE 120, which may be one of the UEs in FIG. 1. On the uplink, data and signaling (e.g., MRMs) to be sent by UE 120 may be processed (e.g., formatted, encoded, and interleaved) by an encoder 1122 and further processed (e.g., modulated, channelized, and scrambled) by a modulator (MOD) 1124 to generate output chips. A transmitter (TMTR) 1132 may condition (e.g., convert to analog, filter, amplify, and frequency upconvert) the output chips and generate an uplink signal, which may be transmitted via an antenna 1134. On the downlink, antenna 1134 may receive downlink signals from Node B 110 and other Node Bs. A receiver (RCVR) 1136 may condition (e.g., filter, amplify, frequency downconvert, and digitize) the received signal from antenna 1134 and provide samples. A demodulator (DEMOD) 1126 may process (e.g., descramble, channelize, and demodulate) the samples and provide symbol estimates. A decoder 1128 may further process (e.g., deinterleave and decode) the symbol estimates and provide decoded data. Encoder 1122, modulator 1124, demodulator 1126, and decoder 1128 may be implemented by a modem processor 1120. These units may perform processing in accordance with the radio technology (e.g., W-CDMA, GSM, CDMA 1X, etc.) utilized by the wireless network. A controller/processor 1140 may direct the operation at UE 120. A memory 1142 may store program codes and data for UE 120.

FIG. 11 also shows a design of Node B 110, network probe 128, and server 132. Node B 110 includes a controller/processor 1150 that performs various functions for communication with the UEs, a memory 1152 that stores program codes and data for Node B 110, and a transmitter/receiver 1154 that supports radio communication with the UEs. Network probe 128 includes a controller/processor 1160 that performs various functions to capture MRMs from the UEs and a memory 1162 that stores program codes and data for network probe 128 and the captured MRMs. Controller/processor 1160 may perform process 1000 in FIG. 10 and/or other processes. Server 132 includes a controller/processor 1170 and a memory 1172. Controller/processor 1170 may perform various functions to process the MRMs to obtain load/traffic maps, RF maps, mobility maps, etc. and/or to determine RF parameters of cells. Memory 1172 may store program codes and data for server 132, various maps, RF parameter settings, etc. Controller/processor 1170 may perform process 300 in FIG. 3, process 400 in FIG. 4, process 800 in FIG. 8, process 1000 in FIG. 10, and/or other processes to determine RF parameters of cells. These processes may also be performed by other network entities.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosure is provided to enable any person skilled in the art to make or use the disclosure. Various modifications to the disclosure will be readily apparent to those skilled in the art, and the generic principles defined herein may be applied to other variations without departing from the scope of the disclosure. Thus, the disclosure is not intended to be limited to the examples and designs described herein but are to be accorded the widest scope consistent with the principles and novel features disclosed herein.

What is claimed is:

1. An apparatus comprising:
at least one processor to obtain a measurement report message (MRM) from a plurality of measurement report messages (MRMs) comprising timing measurements for multiple cells in a wireless communication network, the MRM being sent by a user equipment (UE) for handover or when triggered, and to determine location of the UE, when the MRM is generated, based on the timing measurements in the MRM; and
a memory coupled to the at least one processor,
wherein the at least one processor determines relative time differences (RTDs) for the multiple cells, computes a weighted average for each of the RTDs, and determines the location of the UE based on weighted averages, wherein weights applied to the RTDs are based on a number of the multiple cells in each of the plurality of MRMs.

2. The apparatus of claim 1, wherein the at least one processor determines observed delay differences for the multiple cells based on the timing measurements, and determines the location of the UE further based on the observed delay differences and known locations of the multiple cells.

3. The apparatus of claim 2, wherein the MRM further comprises radio frequency (RF) measurements for the multiple cells, and wherein the at least one processor determines initial values for the RTDs based on the RF measurements.

4. The apparatus of claim 2, wherein the at least one processor determines initial values for the RTDs based on known location of one of the multiple cells.

5. The apparatus of claim 1, wherein the timing measurements comprise system frame number-connection frame number (SFN-CFN) observed time difference measurements.

6. The apparatus of claim 1, wherein the timing measurements comprise system frame number-system frame number (SFN-SFN) observed time difference measurements.

7. A method comprising:
obtaining a measurement report message (MRM) from a plurality of measurement report messages (MRMs) comprising timing measurements for multiple cells in a wireless communication network, the MRM being sent by a user equipment (UE) for handover or when triggered; and
determining location of the UE, when the MRM is generated, based on the timing measurements in the MRM, wherein the determining comprises:
determining relative time differences (RTDs) for the multiple cells;
computing a weighted average for each of the RTDs; and
determining the location of the UE based on weighted averages, wherein weights applied to the RTDs are based on a number of the multiple cells in each of the plurality of MRMs.

8. The method of claim 7, the determining the location of the UE further comprising:
determining observed delay differences for the multiple cells based on the timing measurements, and determining the location of the UE further based on the observed delay differences and known locations of the multiple cells.

9. An apparatus comprising:
means for obtaining a measurement report message (MRM) from a plurality of measurement report messages (MRMs) comprising timing measurements for multiple cells in a wireless communication network, the MRM being sent by a user equipment (UE) for handover or when triggered; and
means for determining location of the UE, when the MRM is generated, based on the timing measurements in the MRM, wherein the means for determining comprises:
means for determining relative time differences (RTDs) for the multiple cells;
means for computing a weighted average for each of the RTDs; and
means for determining the location of the UE based on weighted averages, wherein weights applied to the RTDs are based on a number of the multiple cells in each of the plurality of MRMs.

10. The apparatus of claim 9, the means for determining the location of the UE further comprising:
means for determining observed delay differences for the multiple cells based on the timing measurements, and
means for determining the location of the UE further based on the observed delay differences and known locations of the multiple cells.

11. A non-transitory computer-readable medium storing a computer program, wherein execution of the computer program is for:
obtaining a measurement report message (MRM) from a plurality of measurement report messages (MRMs) comprising timing measurements for multiple cells in a wireless communication network, the MRM being sent by a user equipment (UE) for handover or when triggered; and
determining location of the UE, when the MRM is generated, based on the timing measurements in the MRM by:
determining relative time differences (RTDs) for the multiple cells;
computing a weighted average for each of the RTDs; and
determining the location of the UE based on weighted averages, wherein weights applied to the RTDs are based on a number of the multiple cells in each of the plurality of MRMs.

12. The non-transitory computer-readable medium of claim 11, wherein execution of the computer program is also for:
determining observed delay differences for the multiple cells based on the timing measurements, and
determining the location of the UE further based on the observed delay differences and known locations of the multiple cells.

13. A method comprising:
obtaining measurement report messages (MRMs) from a plurality of user equipments (UEs) in a wireless communication network, wherein each MRM includes timing information for multiple cells in the wireless communication network;
determining locations of the UEs during handover based on the MRMs, wherein a determining of a location of a UE during handover involves: 1) determining relative time differences (RTDs) for multiple cells, 2) computing a weighted average for each of the RTDs, and 3) determining the location of the UE based on the weighted averages, wherein the weights applied to the RTDs are based on a number of the multiple cells in each of the MRMs used in the determining of the location of the UE;
determining mobility information based on the determined locations of the UEs during handover, wherein the mobility information indicates the locations of the UEs during handover; and
using the mobility information to adjust a radio frequency (RF) parameter of at least one cell in the wireless communication network.

* * * * *